(12) United States Patent
Aldayel

(10) Patent No.: US 12,076,354 B2
(45) Date of Patent: Sep. 3, 2024

(54) ANTIBIOTIC WITH SPIRULINA PLATENSIS AND PLANT EXTRACTS

(71) Applicant: KING FAISAL UNIVERSITY, Al-Ahsa (SA)

(72) Inventor: Munirah Fahad Aldayel, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/388,739

(22) Filed: Nov. 10, 2023

(65) Prior Publication Data

US 2024/0091287 A1 Mar. 21, 2024

Related U.S. Application Data

(62) Division of application No. 17/947,793, filed on Sep. 19, 2022.

(51) Int. Cl.
| | |
|---|---|
| *A61K 36/575* | (2006.01) |
| *A61K 35/04* | (2006.01) |
| *A61K 35/748* | (2015.01) |
| *A61K 36/02* | (2006.01) |
| *A61P 31/04* | (2006.01) |
| *C12N 1/12* | (2006.01) |

(52) U.S. Cl.
CPC ............ *A61K 36/02* (2013.01); *A61K 35/04* (2013.01); *A61K 35/748* (2013.01); *A61K 36/575* (2013.01); *A61P 31/04* (2018.01); *C12N 1/125* (2021.05)

(58) Field of Classification Search
None
See application file for complete search history.

(56) References Cited

FOREIGN PATENT DOCUMENTS

| CN | 103371307 A | 10/2013 | | |
|---|---|---|---|---|
| WO | WO-2005065697 A1 | * | 7/2005 | ........... A61K 35/748 |

OTHER PUBLICATIONS

Machine translation of WO 2005065697 A1.*
Mohamed, S., et al., Estimation Of Antibacterial And Antioxidant Activities Of Phycocyanin Isolated From Spirulina, Zagazig J. Agric . Res., vol. 45 No. (2) 2018, 657-66 (Year: 2018).*
Khadke, S.K., et al., Inhibitory Effects of Honokiol and Magnolol on Biofilm Formation by Acinetobacter baumannii, Biotechnology and Bioprocess Engineering 24: 359-365 (2019) (Year: 2019).*
Pandey, P.S., Shilajit—A Wonder Drug of Ayurveda: An Overview, Int. J. Pharm. Sci. Rev. Res., 59(1), Nov.-Dec. 2019; Article No. 23, 140-43 (Year: 2019).*
Sivalingam, Isolation, identification and evaluation of Spirulina platensis for its effect on seed germination of groundnut (*Arachis hypogaea* L.), Wolaita Sodo, Southern Ethiopia, J. Algal Biomass UtIn. 2020, 11(2): 34-42 (Year: 2020).*
Abdel-Moneim, E. A. M., et al., "Antioxidant and antimicrobial activities of Spirulina platensis extracts and biogenic selenium nanoparticles against selected pathogenic bacteria and fungi," Saudi Journal of Biological Sciences, 29(2), Sep. 2021, pp. 1197-1209.
Kloskowski, T., et al., "Mumio (Shilajit) as a potential chemotherapeutic for the urinary bladder cancer treatment," Scientific Reports, 11, Article No. 22614, Nov. 19, 2021.
Lee, J. , et al., "Antibacterial and Anti-inflammatory Effects of a Magnolia Extract," Cosmetics & Toiletries website, Jul. 3, 2013 (https://www.cosmeticsandtoiletries.com/cosmetic-ingredients/actives/article/21836965/antibacterial-and-anti-inflammatory-effects-of-a-magnolia-extract).

* cited by examiner

*Primary Examiner* — H. Sarah Park
(74) *Attorney, Agent, or Firm* — Nath, Goldberg & Meyer; Joshua B. Goldberg

(57) ABSTRACT

An antibiotic with *Spirulina platensis* and plant extracts is an antibiotic composition including a combination of *Spirulina platensis*, an essential oil of *Magnolia officinalis*, and an essential oil of mumie. In an embodiment, the antibiotic composition may be effective in treating *Acinetobacter baumannii* infections. In a further embodiment, the antibiotic composition may be effective in treating multidrug resistant (MDR) and/or extremely drug resistant (XDR) *Acinetobacter baumannii* infections. In an embodiment, the antibiotic composition may be administered to a subject in need thereof to treat or prevent an *Acinetobacter baumannii* infection, such as a MDR or XDR *Acinetobacter baumannii* infection.

1 Claim, No Drawings

ANTIBIOTIC WITH SPIRULINA PLATENSIS AND PLANT EXTRACTS

CROSS-REFERENCE TO RELATED APPLICATION

This application is a divisional of U.S. patent application Ser. No. 17/947,793, filed on Sep. 19, 2022, the entire contents of which are incorporated herein by reference.

BACKGROUND

1. FIELD

The disclosure of the present patent application relates to antibiotics, and particularly, to an antibiotic including *Spirulina platensis* and plant extracts.

2. Description of the Related Art

*Acinetobacter baumannii* is a critical pathogen that can be terminal in human beings, particularly immunocompromised patients in a hospital or other medical setting. *Acinetobacter baumannii* can be particularly dangerous because drug resistant strains of the bacterium have developed, including multidrug resistant strains that can be resistant to all commonly used antibiotics, including aminoglycosides, cephalosporins, carbepenems, extended spectrum penicillins, and quinolones. *Acinetobacter baumannii* can cause infections in the blood, urinary tract, and lungs, or in wounds in any part of the body. It can also colonize in patients without causing symptoms, making it exceedingly difficult to eradicate in medical settings. The rise of multidrug resistant *Acinetobacter baumannii* is considered an urgent threat (CDC 2019 Antibiotic Resistant Threats Report).

Thus, an antibiotic with *Spirulina platensis* and plant extracts for use against *Actinetobacter baumannii* solving the aforementioned problems are desired.

SUMMARY

An antibiotic with *Spirulina platensis* and plant extracts is a composition including *Spirulina platensis* an extract of *Magnolia officinalis*, and an extract of mumie. In an embodiment, the antibiotic composition may be effective in treating *Acinetobacter baumannii* infections. In a further embodiment, the antibiotic composition may be effective in treating multidrug resistant (MDR) and/or extremely drug resistant (XDR) *Acinetobacter baumannii* infections. In an embodiment, the antibiotic composition may be administered to a subject in need thereof to treat or prevent an *Acinetobacter baumannii* infection or a MDR *Acinetobacter baumannii* infection.

An embodiment of the present subject matter is directed to a pharmaceutical composition including *Spirulina platensis*, plant extracts, and a pharmaceutically acceptable carrier.

An embodiment of the present subject matter is directed to a method of making a pharmaceutical composition including mixing the antibiotic with *Spirulina platensis* and plant extracts under sterile conditions with a pharmaceutically acceptable carrier, preservatives, buffers, or propellants to create the pharmaceutical composition; and providing the pharmaceutical composition in a form suitable for daily, weekly, or monthly administration.

An embodiment of the present subject matter is directed to a method of treating *Acinetobacter baumannii* infections, including administering to a subject in need thereof a therapeutically effective amount of a pharmaceutical composition according to the present subject matter.

These and other features of the present subject matter will become readily apparent upon further review of the following specification.

DETAILED DESCRIPTION OF THE PREFERRED EMBODIMENTS

An antibiotic with *Spirulina platensis* and plant extracts is an antibiotic composition including a combination of *Spirulina platensis*, an extract of *Magnolia officinalis*, and an extract of mumie. In an embodiment, the antibiotic composition may be effective in treating *Acinetobacter baumannii* infections. In a further embodiment, the antibiotic composition may be effective in treating multidrug resistant (MDR) and/or extremely drug resistant (XDR) *Acinetobacter baumannii* infections. In an embodiment, the antibiotic composition may be administered to a subject in need thereof to treat or prevent an *Acinetobacter baumannii* infection or a MDR *Acinetobacter baumannii* infection.

Throughout this application, the term "about" may be used to indicate that a value includes the standard deviation of error for the composition, device or method being employed to determine the value.

The use of the term "or" in the specification and claim(s) is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps. In certain cases, the term "comprising" may be replaced with "consisting essentially of" or "consisting of."

The use of the word "a" or "an" when used herein in conjunction with the term "comprising" in the claims and/or the specification may mean "one," but it is also consistent with the meaning of "one or more," "at least one," and "one or more than one."

As used herein, the term "multiple drug resistant", "multidrug resistant", or "MDR" refers to a bacterial strain that it resistant to treatment with more than one class of antibiotic.

As used herein, the term "extensively drug resistant" or "XDR" refers to a bacterial strain that is resistant to treatment with all but two less categories of available antibiotics.

As used herein, "mumie" or "mumie extract" refers to an inorganic semi-solid herbal substance frequently obtained from crevice caves and used to treat bone diseases in traditional medicine. Mumie may also be known as shilojit, moomiyo, mummiyo, and mumio.

An embodiment of the present subject matter is directed to a pharmaceutical composition comprising the antibiotic with *Spirulina platensis* and plant extracts and a pharmaceutically acceptable carrier.

An embodiment of the present subject matter is directed to a method of making a pharmaceutical composition including mixing the antibiotic with *Spirulina platensis* and plant extracts with a pharmaceutically acceptable carrier. For example, the method of making a pharmaceutical composition can include mixing the antibiotic with *Spirulina platensis* and plant extracts under sterile conditions with a pharmaceutically acceptable carrier, preservatives, buffers, and/or propellants to create the pharmaceutical composition.

An embodiment of the present subject matter is directed to a pharmaceutical composition including the antibiotic with *Spirulina platensis* and plant extracts. To prepare the pharmaceutical composition, the antibiotic with *Spirulina platensis* and plant extracts, as an active ingredient, is intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral, parenteral, intranasal, sublingual or rectal administration, or for administration by inhalation or insufflation. The active compound can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of the antibiotic with *Spirulina platensis* and plant extracts or an amount effective to treat a disease, such as a disease associated with *Acinetobacter baumanii*, may be determined initially from the Examples described herein and adjusted for specific targeted diseases using routine methods.

The antibiotic with *Spirulina platensis* and plant extracts can be administered to a subject in need thereof. For example, the antibiotic composition can be used to treat a subject suffering from a disease associated with *Acinetobacter baumannii*. The disease can be caused by MDR *Acinetobacter baumannii* or XDR *Acinetobacter baumannii*.

An embodiment of the present subject matter is directed to a method of treating *Acinetobacter baumannii*, comprising administering to a subject in need thereof a therapeutically effective amount of the pharmaceutical composition according to the present subject matter.

The antibiotic with *Spirulina platensis* and plant extracts or pharmaceutical compositions thereof can be administered to a subject by any suitable route. For example, the compositions can be administered orally (including bucally and sublingually), nasally, rectally, intracisternally, intra vaginally, intraperitoneally, topically, transdermally (as by powders, ointments, or drops), and/or parenterally. As used herein, "parenteral" administration refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation may also be contemplated, including, for example, embedding a composition of the disclosure in the body such as, for example, in a tissue, in the abdominal cavity, under the splenic capsule, brain, or in the cornea.

Accordingly, the route of administration can include intranasal administration, oral administration, inhalation administration, subcutaneous administration, transdermal administration, intradermal administration, intra-arterial administration with or without occlusion, intracranial administration, intraventricular administration, intravenous administration, buccal administration, intraperitoneal administration, intraocular administration, intramuscular administration, implantation administration, topical administration, intratumor administration, and/or central venous administration.

In an embodiment, the antibiotic with *Spirulina platensis* and plant extracts may comprise *Spirulina platensis* extracts and essential oils of *Magnolia officinalis* and mumie. In a further embodiment, the antibiotic with *Spirulina platensis* and plant extracts may comprise about 1 ml *Spirulina platensis* extract, about 1 ml 100% pure essential oil of *Magnolia officinalis* and about 1 ml 100% pure essential oil of mumie.

In an embodiment, the *Spirulina platensis* extract may be isolated by collecting water samples from marine freshwater habitats, isolating and culturing marine cyanobacteria by culturing on F/2 medium, and using Bold's medium for brackish cyanobacteria. The resulting cyanobacteria cultures may be purified, and about 0.5 g of fresh biomass may be ground in about 5 ml, centrifuged to remove solid waste, and condensed to about 1 ml. The following examples illustrate the present subject matter.

Example 1

Isolation and Purification of *Spirulina platensis* Extract

Water samples were collected from marine (AL Uqair coast, Eastern Province, Al Ahsa, Kingdom of Saudi Arabia) and freshwater habitats (canals fed from underground brackish water, Al Ahsa, Kingdom of Saudi Arabia). The samples were examined using light microscopy and cyanobacterial cells were isolated and cultured using F/2 medium for marine cyanobacteria according to methods previously reported by Guillard and Ryther (Insert Full Ref 1962) and using Bold's medium for brackish cyanobacteria according to methods previously reported by Stein (Insert Full Ref 1980). Cyanobacterial cultures were purified according to standard techniques and monospecific cultures were established. About 0.5 g of fresh biomass was ground in 5 ml water and centrifuged, the resulting extract was isolated and condensed to 1 ml.

Example 2

Synthesis of Antibiotic Compositions

*Spirulina platensis* extracts (1 ml) synthesized according to Example 1 were combined with 100% pure essential oils of *Magnolia officinalis* and mumie (1 ml each) to produce an antibiotic composition.

The antibiotic composition was tested using the disk diffusion susceptibility method previously published by Bauer et al. (Bauer, A. W., et al., "Antibiotic susceptibility testing by a standardized single disk method," Amer J Clin Pathol 45: pp. 495-496 (1996)). Briefly, a multidrug resistant strain of *Acinetobacter baumannii* was isolated from patients with Type 2 Diabetes Mellitus in a hospital setting in Saudi Arabia. Whatman No. 1 sterilized-paper disks were saturated with 20 µl of the antibiotic composition. Disks were then dried and placed on the surface of a medium inoculated with either the isolated MDR *Acinetobacter baumannii* or *Acinetobacter baumannii* (ATCC17978). A further test was run using either 10 µg colistin or 15 µg Tigecycline as controls. The plates containing the inoculated medium were kept for 2 hours at 4° C. to ensure the diffusion of the bioactive material, and then were incubated at 37° C. Disks containing 30 µl of water were used as a negative control. Significant zones of inhibition were observed around the tested antibiotic composition, but not around the traditional antibiotic controls, confirming that the strains of *Acinetobacter baumannii* tested were resistant to traditional antibiotics, but susceptible to the antibiotic compositions discussed herein.

It is to be understood that the antibiotic with *Spirulina platensis* and plant extracts is not limited to the specific embodiments described above but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method of making an antibiotic composition effective to inhibit the growth of a strain of *Acinetobacter baumannii* selected from the group consisting of MDR *Acinetobacter baumannii* and XDR *Acinetobacter baumannii*, the method comprising combining equal parts of a *Spirulina platensis* extract, an essential oil of *Magnolia officinalis*, and an essential oil of mumie, wherein the *Spirulina platensis* extract is obtained by:

(a) collecting a water sample from an environment selected from the group consisting of a marine environment and a brackish environment;

(b) isolating cyanobacterial cells from the water sample;

(c) growing the cyanobacterial cells on a medium selected from the group consisting of a F/2 medium and Bold's medium;

(d) establishing a monospecific culture using the cyanobacterial cells;

(e) obtaining a biomass of the monospecific culture;

(f) grinding the biomass in water; and (g) centrifuging the ground biomass to remove solids to obtain a first extract; and (h) concentrating the centrifuged biomass first extract to obtain the *Spirulina platensis* extract.

* * * * *